(12) United States Patent
Wang et al.

(10) Patent No.: US 9,603,518 B2
(45) Date of Patent: Mar. 28, 2017

(54) OPTICAL MEASURING DEVICE AND METHOD

(71) Applicant: CRYSTALVUE MEDICAL CORPORATION, Taoyuan (TW)

(72) Inventors: Kuo-Jen Wang, Taoyuan (TW); Chun-Nan Lin, Taoyuan (TW)

(73) Assignee: CRYSTALVUE MEDICAL CORPORATION, Taoyuan (TW)

( * ) Notice: Subject to any disclaimer, the term of this patent is extended or adjusted under 35 U.S.C. 154(b) by 33 days.

(21) Appl. No.: 14/831,850

(22) Filed: Aug. 20, 2015

(65) Prior Publication Data

US 2016/0051138 A1 Feb. 25, 2016

(30) Foreign Application Priority Data

Aug. 20, 2014 (TW) .............................. 103128688 A (51) Int. Cl.
*A61B 3/14* (2006.01)
*A61B 3/10* (2006.01)
*G02B 26/10* (2006.01)
*A61B 3/00* (2006.01)
*A61B 3/15* (2006.01)

(52) U.S. Cl.
CPC ............ *A61B 3/102* (2013.01); *A61B 3/0025* (2013.01); *A61B 3/1005* (2013.01); *A61B 3/152* (2013.01); *G02B 26/105* (2013.01)

(58) Field of Classification Search
CPC ........ A61B 1/00172; A61B 2562/0242; A61B 3/102; A61B 5/0064; A61B 5/0066; A61B 5/0068; G01B 11/2441; G01B 2290/45; G01B 2290/65; G01B 9/02027
USPC ......................................... 351/205, 206, 208
See application file for complete search history.

(56) References Cited

U.S. PATENT DOCUMENTS

5,459,570 A 10/1995 Swanson et al.

*Primary Examiner* — Mahidere Sahle
(74) *Attorney, Agent, or Firm* — Cheng-Ju Chiang (57) ABSTRACT

An optical measuring device is provided. An actuator of a reference mirror set drives a reference mirror to move back and forth at a scan velocity. A first light source module transmits a first light beam to an optical coupling module transmitting two parts of the first light beam respectively to an examinee object and the reference mirror set. The first light beam then is reflected by the examinee object and reference mirror set and then transmitted to the optical coupling module and the processing unit. The second light source module transmits a second light beam to the examinee object. Then the second light beam is reflected and then transmitted to the second sensing unit. The second sensing unit provides a sensing signal to the processing unit which accordingly provides a value of the relative velocity. The thickness is calculated according to the relative velocity and the scan velocity.

9 Claims, 4 Drawing Sheets

OPTICAL MEASURING DEVICE AND METHOD

CROSS REFERENCE TO RELATED APPLICATIONS

This Non-provisional application claims priority under 35 U.S.C. §119(a) on Patent Application No(s). 103128688 filed in Taiwan, Republic of China on Aug. 20, 2014, the entire contents of which are hereby incorporated by reference.

BACKGROUND

Technical Field

The invention relates to an optical measuring device and method.

Related Art

Because optical measuring device is non-invasive and quick responsive, etc, it is usually applied to contactless detection. For example, it can be applied to detect the inside structure of eyeball or subcutaneous tissue. However, regardless of what kinds of optical measuring technology, problems of measuring error caused by the measuring device, the examinee's physiological response or the examinee's movement still occurs.

As to the cornea measuring device by optical coherence tomography, two solutions to avoid the above mentioned error are provided. One solution accelerates the measuring scan time to eliminate effects by vibration during measuring. Alternatively, by installing two sets of light source modules in the measuring device, two light modules can simultaneously produce two light beams which both perform optical coherence interference so as to correct the relative vibration between the device and the cornea. But the former solution, even the scan time is shortened, still suffers a condition that the relative movement between the device and the examinee object interferes the measuring result, and it is also technically difficult to improve scan time on the measuring device. The optical path of the latter solution is more complicated, and installing additional light source module will make the cost increased.

Therefore, it is an important subject in the field to provide a method and a device which can eliminate or abate the error caused by the relative movement between the device and the examinee object during measuring process.

SUMMARY

In view of the above subject, an objective of the invention is to provide an optical measuring device and method with corrected optical measurement. Further, utilizing the device and method of the invention can lower the error during measuring process.

To achieve the above objective, the invention provide an optical measuring device including a first light source module, a second light source module, a first sensing unit, a second sensing unit, a reference mirror set, an optical coupling module and a processing unit.

The first light source module provides a first light beam and the second light source module provides a second light beam. The reference mirror set has an actuator and a reference mirror. The actuator drives the reference mirror to move back and forth at a scan velocity. The optical coupling module transmits the first light beam to the reference mirror set and an examinee object.

The first light source module transmits the first light beam to the optical coupling module. The optical coupling module transmits one part of the first light beam to the examinee object, and the other one part of the first light beam to the reference mirror set. The one part of the first light beam is reflected by the surface of the examinee object and then transmitted to the optical coupling module, the first sensing unit and the processing unit in sequence, the other one part of the first light beam is reflected by the reference mirror set and then transmitted to the optical coupling module, the first sensing unit and the processing unit in sequence.

The second light source module transmits a second light beam to the examinee object, the second light beam is reflected by the surface of the examinee object and then transmitted to the second sensing unit. The second sensing unit accordingly provides a sensing signal to the processing unit. The processing unit provides a value of the relative velocity according to the sensing signal. A thickness is calculated according to the value of the relative velocity and the scan velocity of the reference mirror set.

In one embodiment, the thickness is generated according to the integration of the fraction being the sum of the scan velocity and the value of the relative velocity with respect to the refractive index of the examinee object.

In one embodiment, the processing unit utilizes the following formula to calculate the thickness:

$$L = \int_0^T \frac{Vr + Vs}{n} dt$$

wherein $V_r$ represents the scan velocity, $V_S$ represents the value of the relative velocity, n represents the refractive index of the examinee object.

In one embodiment, the processing unit utilizes the following formula to calculate the thickness:

$$L = \int_0^T \frac{Vr}{n} * \left\{ 1 + \left( \sqrt{\frac{1+\beta}{1-\beta}} - 1 \right) / n \right\} dt$$

$$\beta = \frac{n * Vs}{Vr}$$

wherein $V_r$ represents the scan velocity, $V_S$ represents the value of the relative velocity, n represents the refractive index of the examinee object.

In one embodiment, during a first time sequence, the first light beam reflected by the examinee object and the first light beam reflected by the reference mirror set produce constructive interference, and the processing unit accordingly provides a first optical path difference. During a second time sequence, the first light beam reflected by the examinee object and the first light beam reflected by the reference mirror set produce constructive interference, and the processing unit accordingly provides a second optical path difference. Thus, the processing unit calculates the time interval between the first time sequence and the second time sequence according to the first and the second optical path differences.

The invention provides an optical measuring method for an optical measuring device of which a reference mirror set has a scan velocity. The method includes the steps of: providing a light beam to a surface of an examinee object; reflecting the light beam by the surface of the examinee object and then being transmitted to a sensing unit; transmitting a sensing signal to a processing unit by the sensing unit, wherein the sensing signal includes information about the scanning velocity of the light beam; providing a value of relative velocity between the optical measuring device and the surface of the examinee object according to the sensing signal by the processing unit; and calculating a thickness of the examinee object according to the value of the relative velocity and the scan velocity of the reference mirror set.

In one embodiment, the method further includes a step of calculating the thickness according to the integration of the fraction being the sum of the scan velocity and the value of the relative velocity with respect to the refractive index of the examinee object.

In one embodiment, the thickness L is:

$$L = \int_0^T \frac{Vr + Vs}{n} dt$$

wherein $V_r$ represents the scan velocity, $V_S$ represents the value of the relative velocity, n represents the refractive index of the examinee object.

In one embodiment, the thickness L is:

$$L = \int_0^T \frac{Vr}{n} * \left\{ 1 + \left( \sqrt{\frac{1+\beta}{1-\beta}} - 1 \right) \middle/ n \right\} dt$$

$$\beta = \frac{n * Vs}{Vr}$$

wherein $V_r$ represents the scan velocity, $V_S$ represents the value of the relative velocity, n represents the refractive index of the examinee object.

In summary, the invention can calculate the value of the relative velocity between the optical measuring device and the examinee object by the light source module and the sensing unit, and calculate the thickness of the examinee object according to the scan velocity of the reference mirror set and the relative velocity. By way of the correction, it can eliminate or abate the effect from the relative vibration between the optical measuring device and the examinee object and the effect from the environmental disturbance on measurement precision during measurement process, thus achieving the objective of improving measurement precision.

Besides, according to the invention, it is not necessary to install or design additional anti-vibration structure on the optical measuring device. Thus, it simplifies the design of the optical measuring device and lowers the cost. Furthermore, the invention can perform measurement and correction based on the existing framework of the optical measuring device. It merely needs to introduce correction into the processing unit but it outstandingly improves measurement precision on condition that no additional correction unit is necessary to install and no existing device will be replaced. Thus, it is beneficial and effective.

BRIEF DESCRIPTION OF THE DRAWINGS

The embodiments will become more fully understood from the detailed description and accompanying drawings, which are given for illustration only, and thus are not limitative of the present invention, and wherein.

DETAILED DESCRIPTION OF THE INVENTION

An optical measuring device and method according to embodiments of the present invention will be apparent from the following detailed description, which proceeds with reference to the accompanying drawings, wherein the same references relate to the same elements. In the following embodiments and drawings, the elements and steps which are not directly relative to the invention are omitted and not shown. The dimension relationship between each element in the drawings is used for simply understanding, but not used to limit their actual proportion.

Figure 1:
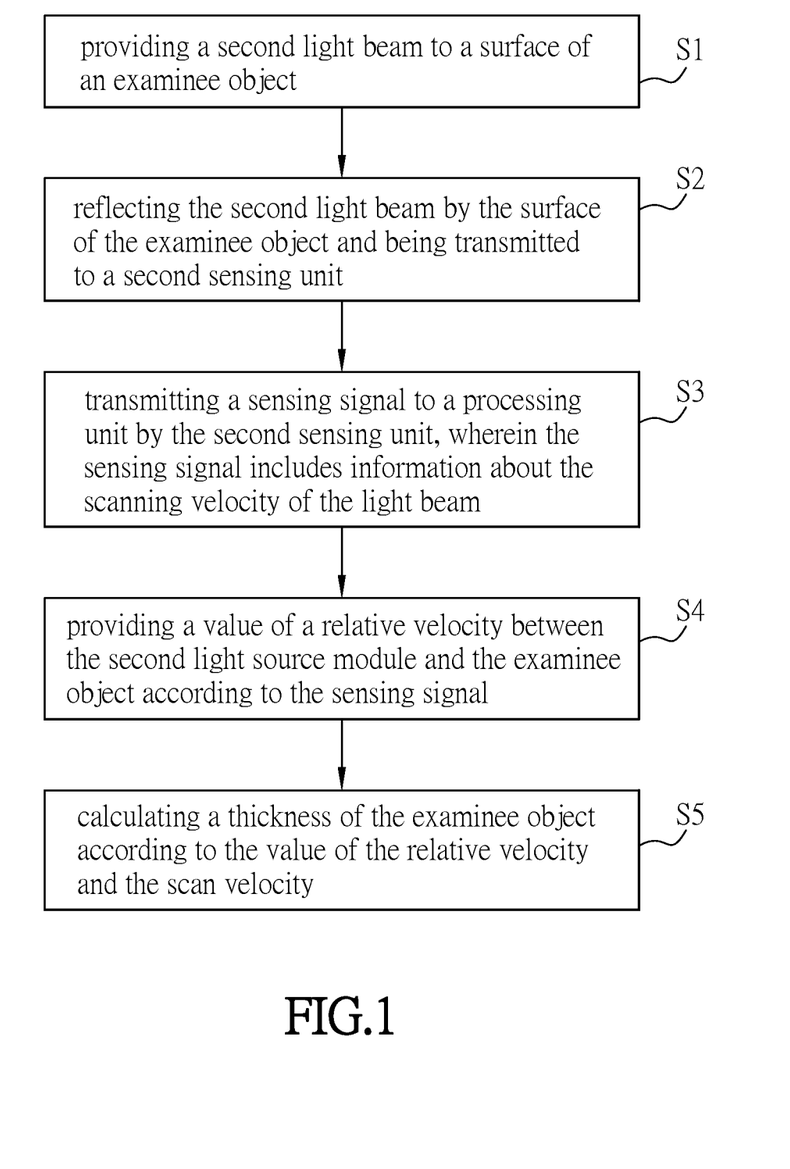
FIG. 1 is a flow chart showing the optical measuring method according to one embodiment of the invention.
Figure 2:
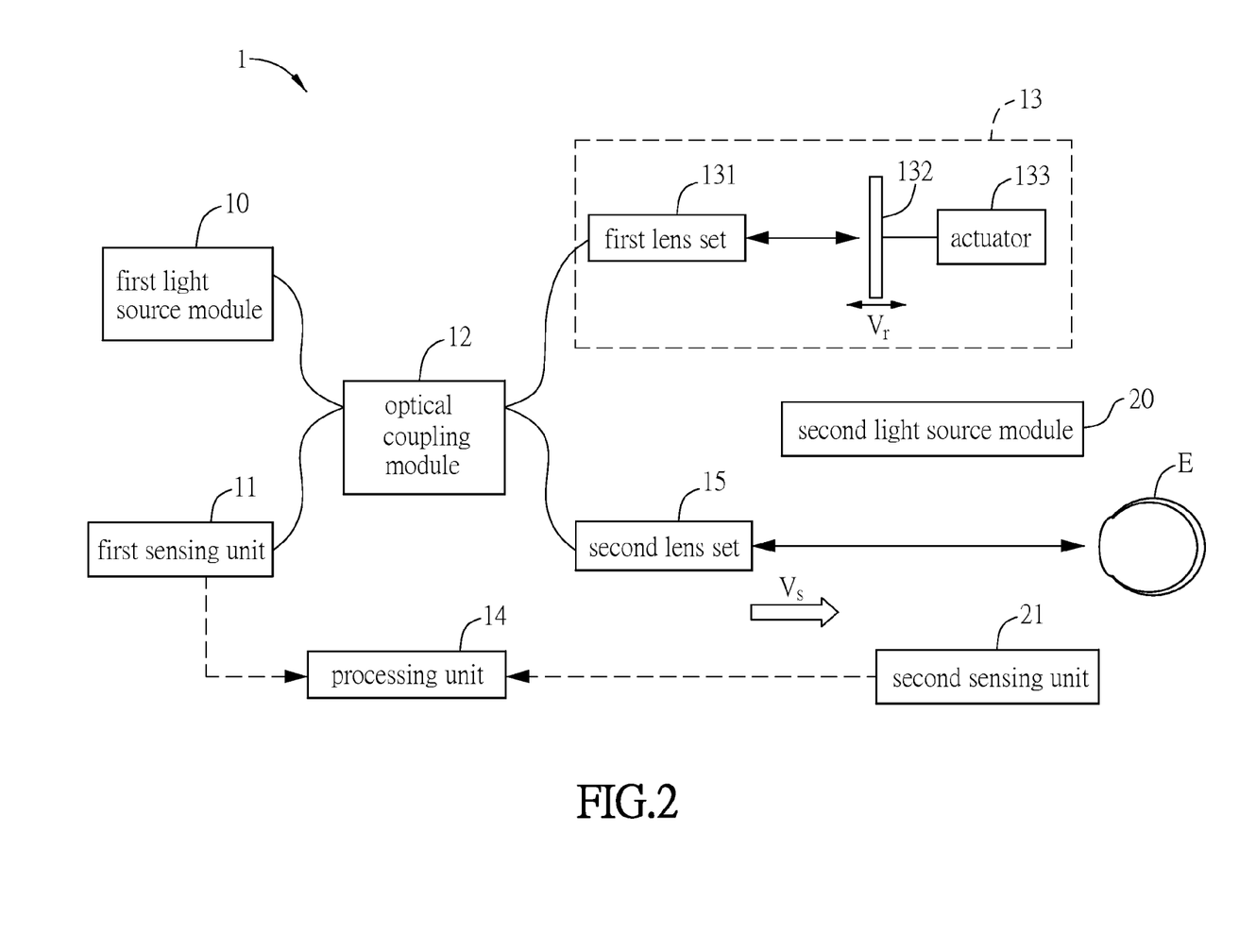
FIG. 2 is a schematic diagram showing the framework of the optical measuring device.
Figure 3:
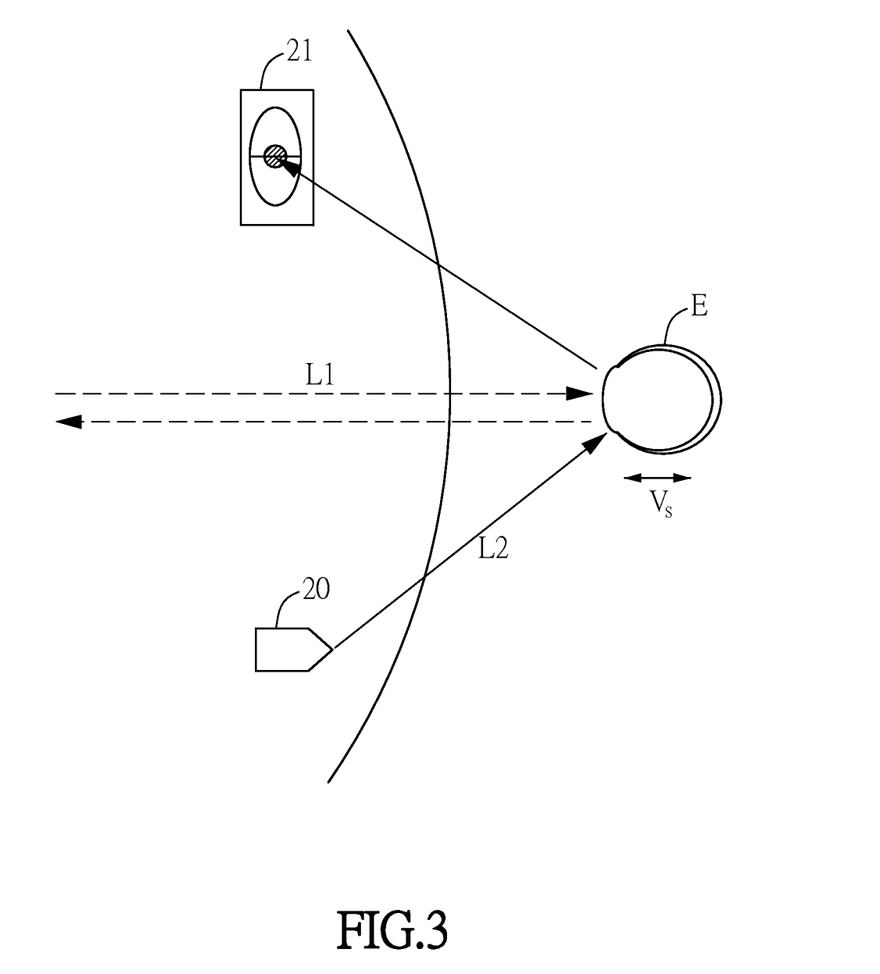
FIG. 3 is a schematic diagram showing the application of the second light source module and the second sensing unit of the optical measuring device.
Figure 4:
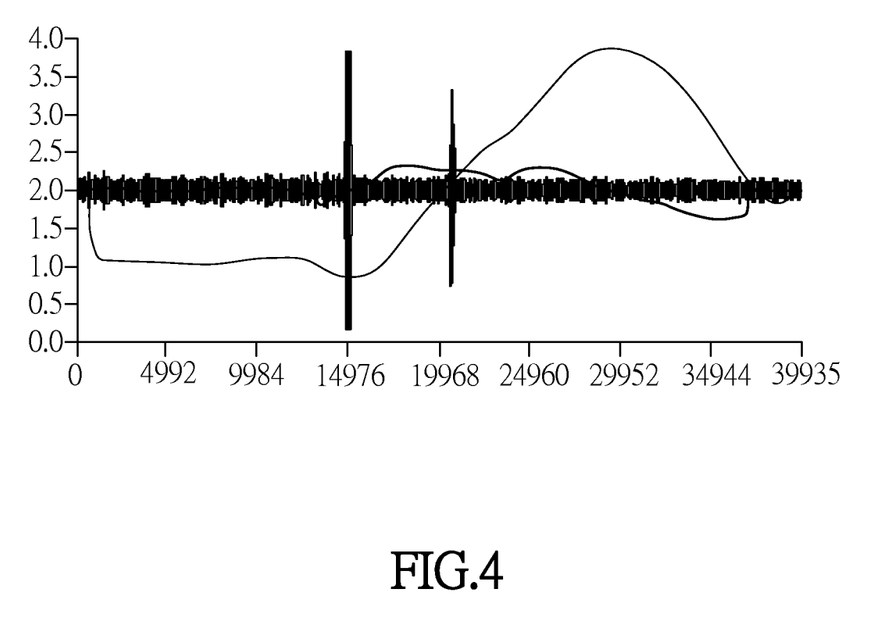
FIG. 4 is a schematic diagram showing the measurement result by the second sensing unit.

Referring to FIGS. 1-4, FIG. 1 is a flow chart showing the optical measuring method according to one embodiment of the invention, FIG. 2 is a schematic diagram showing the framework of the optical measuring device, FIG. 3 is a schematic diagram showing the application of the second light source module the second sensing unit of the optical measuring device, and FIG. 4 is a schematic diagram showing the measurement result by the second sensing unit. For clear illustration, FIG. 2 does not show the second light source module and the second sensing unit of the optical measuring device.

An optical measuring device 1 according to the embodiment includes a first light source module 10, a second light source module 20, a first sensing unit 11, an optical coupling module 12, a reference mirror set 13 and a processing unit 14.

The first light source module 10 and the second light source module 20 respectively provide a first light beam L1 and a second light beam L2. On condition for measuring cornea or retina of human eye and regarding for comforting measured person, the first light source module 10 and the second light source module 20 can be a wide-band laser light source (for instance in the embodiment, the center wavelength of the light source can be 1030 nm and bandwidth can be 20-40 nm, but it is not limited as invisible light). The wide-band laser light source can be provided by emitting narrowband laser into photoluminescence material.

The reference mirror set 13 at least includes an actuator 133 (e.g. micro-actuator) and a reference mirror 132. The reference mirror 132 is driven by the actuator 133 to move back and forth (for instance via a transmission platform not shown in figures). The actuator 133 drives the reference mirror 132 to move at a scan velocity $V_r$. The actual speed of the scan velocity can be obtained from the conversion of the motor revolution. Furthermore, the reference mirror 132 and the actuator 133 can be two independent components or integrated into a single one component (for example attaching the reference mirror 132 to the actuator 133).

The optical coupling module 12 can transmit the first light beam L1 of the first light source module 10 to the reference mirror set 13 and an examinee object E. The optical coupling module 12 transmits one part of the first light beam L1 to the reference mirror set 13, and transmits the other one part of the first light beam L1 to the examinee object E. In the embodiment, the optical coupling module 12 can be a beam splitter but it is not limited. For example, 50% of the light beam from the first light source module 10 can be reflected into the reference mirror set 13, and other 50% of the light beam can be transmitted into the examinee object E so as to have an effect of optical coupling.

Besides, the reference mirror set 13 further includes a first lens set 131 which is composed of at least one lens. It can transmit the first light beam L1 transmitted by the optical coupling module 12 to the reference mirror 132. The optical measuring device 1 in the embodiment may further includes a second lens set 15, by which the first light beam L1 transmitted by the optical coupling module is transmitted to the examinee object E.

Then, the reference mirror set 13 and the examinee object E respectively reflect the first light beam L1. The first light beam L1 exiting from the reference mirror set 13 passes through the first lens set 131, the optical coupling module 12 and the first sensing unit 11 in sequence, and then enters the processing unit 14. The first light beam L1 exiting from the examinee object E passes through the second lens set 15, the optical coupling module 12 and the first sensing unit 11 in sequence, and then enters the processing unit 14. The first sensing unit 11 can transform the light signal into an electrical signal and provide it for the processing unit 14.

Besides, the examinee object E in the embodiment is a spheroid such as an eyeball for illustration, but it is not limited to eyeball measurement. One skilled in the art can utilize the design and concept of the invention to apply to other kinds of examinee objects. As previously mentioned, taking measuring the cornea of the eyeball for example, during a first time sequence, the second lens set 15 is firstly adjusted to concentrate the first light beam L1 on the outer surface of the cornea. At the moment, the actuator 133 drives the reference mirror 132 to move back and forth. When the optical path difference resulted from the first light beam L1 reflected by the reference mirror set 13 is a multiple of the optical path difference resulted from the first light beam L1 reflected by the examinee object E, the first light beams L1 produce constructive interference. Then record the optical path difference and define it as a first optical path difference.

Then, during a second time sequence, the second lens set 15 is adjusted again to concentrate the first light beam L1 on the inner surface of the cornea. Repeating the above steps to let the optical path difference resulted from the first light beam L1 reflected by the reference mirror set 13 be a multiple of the optical path difference resulted from the first light beam L1 reflected by the examinee object E, and the first light beams L1 produce constructive interference. At the moment, record it as a second optical path difference. The processing unit 14 figures out how much time the first light beam L1 moves in the examinee object E according to the two optical path differences (namely, the processing unit 14 accordingly calculates the time interval between the first time sequence and the second time sequence.

Referring to FIG. 2, in the embodiment, the surface of the examinee object E is provided with the light (step S1). In detail, the second light source module 20 provides a second light beam L2 to the surface of the examinee object. The second light beam L2 is reflected by the surface of the examinee object E and then transmitted to the second sensing unit 21 (step S2). Taking cornea measurement for example, the second light beam 12 is transmitted to and then reflected by the outer surface of the cornea.

The second sensing unit 21 is an optical sensing unit, such as PSD (position sensitive detector). The relative position between the examinee object E and the second light source module 20 is measured by the second sensing unit 21 to calculate the relative vibration between the examinee object E or the optical measuring device 1. Taking cornea measurement for example, the second sensing unit 21 can measure the variation of working platform or eye blink.

In detail, the second sensing unit 21 transmits a sensing signal to the processing unit 14, and the sensing signal includes information about the scanning velocity of the light beam (step S3). The processing unit 14 provides the value of the relative velocity between the second light source module 20 and the examinee object E according to the sensing signal. In detail, the second sensing unit 21 transforms the position, which the second light beam L2 focus into, to a sensing signal being transmitted to the processing unit 14. Thus, the processing unit 14 can realize during a unit time period the movement variation of the second light beam L2 (a signal of position to time initially sensed by the second sensing unit 21). After processing the unnecessary optical noise by low-pass filtering, its first derivative is taken with respect to time to obtain the scanning velocity of the light beam (FIG. 4). Herein the scanning velocity of the light beam refers to the relative velocity $V_S$ of the examinee object E to the optical measuring device 1, or represents the relative vibration between the examinee object E to the optical measuring device 1 else.

Hereinafter the calculation and correction to the thickness L will be illustrated.

The correction formula in the embodiment utilizes Doppler formula to perform correction. Because light is a wave with high propagation speed, not only the relative movement between the wave source (the first light source module 10) and the observer (optical measuring device 1), but the effect resulting from the special theory of relativity also takes into considerations. In the embodiment, the moving velocity of the wave source is equal to the wavefront velocity provided by the first light source module 10, namely the scan velocity $V_r$ (the velocity of the reference arm). The moving velocity of the observer (optical measuring device 1) is equal to the product $(n^*V_S)$ of the refractive index of the examinee object E and the relative velocity $V_S$.

Besides, the reason of optical coherence interference is that the optical paths of the reference arm and the sample arm are the same thus producing interference. But the interference will not change accordingly to the moving velocity of the wave source. Thus, it still complies with the covariant with respect to Lorentz transformation. Assuming that the propagation speed of the wavefront of the coherent optical-path-length wave is unchanged and the scan velocity $V_S$ is at a constant speed, it needs correction for the covariant with respect to Lorentz transformation when the propagation speed of the wavefront of the coherent optical-path-length wave approaches to the scan velocity $V_r$.

Moreover, it may refer the scan velocity $V_r$ (the moving velocity of the optical-path-length wavefront of the first light source module 10) similarly to the moving velocity of the wave source of Doppler effect. The $n^*V_S$ is the equivalent optical-path-length wavefront speed that the relative vibrating velocity $V_S$ is at a refractive index n with respect to air medium, and thus it can be realized to the moving velocity of the observer of Doppler effect.

The factors effecting on the thickness L in the optical measuring device 1 at least have: the vibration of the first light source module 10 and the examinee object E. Regardless of the vibration caused from both, the first optical path difference is recorded at time sequence T=0, and the second optical path difference is recorded at time sequence T=T. It can presume that the thickness L of the examinee object E is $V_r/n^*T$, namely, the wavefront moves in the sample at speed $V_r/n$ and its moving time is T (unit time). The product of the two is the thickness L of the examinee object E.

Then, assuming that the first light source module 10 vibrates so as to move at velocity $V_S$ and the examinee object E does not vibrate, it needs to correct the formula to calculate the thickness L as follow:

$$L = \frac{V_r + V_S}{n} * T$$
$$= \frac{V_r}{n} * \left(1 + \frac{V_S}{V_r}\right) * T = \frac{V_r}{n} * \left(1 + \frac{\beta}{n}\right) * T$$
$$\beta = \frac{n * V_S}{V_r}$$

Therefore, in regard to the vibrating velocity $V_S$ of the first light source module 10, the wavefront will move at the speed of $(V_r+V_S)/n$ in time period T in the sample. By arranging the formula again, the above corrected formula can be thus obtained.

Then, assuming again that the first light source module 10 does not vibrate and the examinee object E vibrates so as to move at velocity $V_S$, in this condition, the wavefront will also move at the speed of $(V_r+V_S)/n$ (the same with the previous condition that the first light source module 10 vibrates and the examinee object E does not vibrate). In other words, only the relative vibration between the first light source module 10 and the examinee object E are required for consideration to calculate the thickness L, and it is not necessary to specially perform correction on respective vibration.

As mentioned above, the thickness L is calculated according to the value of the relative velocity $V_S$ and the scan velocity $V_r$ of the reference mirror set (step S5). The thickness L is represented as the following formula (hereinafter call this formula the "normal formula"):

$$L = \int_0^T \frac{Vr}{n} * \left\{1 + \left(\sqrt{\frac{1+\beta}{1-\beta}} - 1\right)/n\right\} dt$$
$$\beta = \frac{n * V_S}{Vr}$$

β is the corrected velocity ratio of Doppler formula (the velocity ratio of the observer of the optical-path-length wavefront to the wave source). When β is much smaller than 1 (the scan velocity $V_r$ is much larger than the value of the relative velocity $V_S$), the formula of thickness L can be simplified as the integration of the fraction which is the sum of the scan velocity $V_r$ and the value of the relative velocity $V_S$ with respect to the refractive index n of the examinee object. The correction formula of the thickness L can be simplified as follow: (hereinafter call this formula the "simplified formula"):

$$L = \int_0^T \frac{Vr + Vs}{n} dt$$

Besides, when the relative velocity $V_S$ is a function of time, β can develop into β(t) which is a function of time. In this condition, it adjusts the correction formula of the thickness L as follow:

$$L = \int_0^T \frac{Vr}{n} * \{1 + \beta(t)/n\} dt = \frac{Vr}{n} \int_0^T \{1 + \beta(t)/n\} dt$$

The thickness L by the above correction will further approach the actual thickness.

Furthermore, the assumption which needs to introduce the theory of relativity for correction in the embodiment is that: according to the special theory of relativity, in the two space-time coordinates between which relative movement exists, if their representation of physical phenomena comply with the covariant with respect to Lorentz transformation, it presumes that the speed of light is constant in the two space-time coordinates. Based on the assumption, although the scan velocity $V_r$ in the embodiment is much smaller than the speed of light, the propagation speeds of coherent optical-path-length wave in the two inertial frames which move relatively are changeless. It is seen from FIG. 4 that when performing scan at constant scan velocity $V_r$, the observed scan velocity $V_r$ by the observer is changeless. Conversely, it presumes that the physical phenomena will comply with the covariant with respect to Lorentz transformation. Thus, it is necessary to apply the correction for the covariant with respect to Lorentz transformation.

As mentioned previously, the optical-path-length wave in the embodiment can be compared to the light of the theory of relativity, the wavefront speed $V_r/n$ of the examinee object can be compared to c (the speed of light) of the theory of relativity, the value of the relative velocity $V_S$ in the embodiment can be compared to the relative velocity between the observer and the wave source of the theory of relativity, $\beta=n* V_S/V_r$ can be compared to the v/c of the theory of relativity. When β is not much smaller than 1, the calculation formula needs to rewrite for overall light transmission to comply with the covariant with respect to Lorentz transformation.

$$L = \int_0^T \frac{Vr}{n} * \{1 + \beta(t)/n\} dt$$
$$= \frac{Vr}{n} \int_0^T \{1 + [(1+\beta) - 1]/n\} dt$$
$$= \frac{Vr}{n} \int_0^T \left\{1 + \left[\frac{(1+\beta)}{\sqrt{(1-\beta^2)}} - 1\right]/n\right\} dt$$

From the above calculation, $(1+\beta)/\sqrt{(1-\beta 2)}$ is the effect of time dilation resulting from Lorentz transformation. On condition that β is small enough, the formula can be simplified into the below formula:

$$L = \int_0^T \frac{Vr}{n} * \left\{1 + \left(\sqrt{\frac{1+\beta}{1-\beta}} - 1\right)/n\right\} dt$$

The optical measuring device in the embodiment at least has the following advantages. On condition that no existing measuring device needs to replace, the measurement precision is improved so that the cost to upgrade the hardware device is eliminated. Because the correction method takes the relative vibration between the measuring device and the examinee object into consideration, the measuring device will be more insusceptible to environmental disturbance during measurement process. The measuring device into which the correction method is introduced will be less limited to the design of installed position or anti-vibration structure. Besides, it also makes operations by human less effective on measurement result. Therefore, an optical measuring device which is easy for operators to operate and of which the operation requirement is lower is provided.

Referring to the below table, the operative condition of the experiment is: the actuator 133 rotates at 800 pps to drive the reference mirror (the scan velocity $V_r$ is 100 mm/s), the refractive index n of the examinee object E is 1.9. When no correction is applied, three measurement results of the thickness of the examinee object (the examinee object is cornea) are 381.6 µm, 304.6 µm and 440.1 µm respectively, and their standard deviation is 68 µm. From the table it is clear that the standard deviation can be reduced by applying the simplified formula for correction (only performing correction for Doppler effect) or applying normal formula (regarding both corrections for Doppler effect and the theory of relativity). In other words, the measurement result by correction will be more insusceptible to the relative vibration of the examinee object E to the first light source module 10.

| Scan velocity $V_r$ = 100 mm/s | Exp. 1 | Exp. 2 | Exp. 3 | S |
|---|---|---|---|---|
| No Correction | 381.6 | 304.6 | 440.1 | 68.0 |
| Simplified Formula ($\beta \ll 1$) | 401.2 | 370.8 | 386.5 | 15.2 |
| Normal Formula | 402.4 | 403.8 | 401.1 | 1.4 |

Following shows the measurement results at different scan velocities. From the corrected results, introduced correction really reduces the influence of the relative vibration of the examinee object E to the first light source module 10.

| | Exp. 1 | Exp. 2 | Exp. 3 | S |
|---|---|---|---|---|
| Scan velocity $V_r$ = 62.5 mm/s | | | | |
| No Correction | 494.2 | 423.4 | 315.0 | 90.3 |
| Simplified Formula ($\beta \ll 1$) | 378.6 | 399.6 | 373.0 | 14.0 |
| Normal Formula | 397.5 | 401.8 | 398.2 | 2.3 |
| Scan velocity $V_r$ = 37.5 mm/s | | | | |
| No Correction | 337.4 | 497.1 | 442.6 | 81.2 |
| Simplified Formula ($\beta \ll 1$) | 366.2 | 399.2 | 410.2 | 22.9 |
| Normal Formula | 407.5 | 418.3 | 415.0 | 5.5 |

Although the above example takes eyeball measurement for illustration, the embodiment may be applied to the measurement of the cornea thickness and the thickness of the retina, etc., and further applied to the thickness measurement of any light transmissible medium (for example, measurement of capillaries under the skin).

In summary, the invention can calculate the value of the relative velocity between the optical measuring device and the examinee object by the light source module and the sensing unit, and calculate the thickness of the examinee object according to the scan velocity of the reference mirror set and the relative velocity. By way of the correction, it can eliminate or abate the effect from the relative vibration between the optical measuring device and the examinee object and the effect from the environmental disturbance on measurement precision during measurement process, thus achieving the objective of improving measurement precision.

Besides, according to the invention, it is not necessary to install or design additional anti-vibration structure on the optical measuring device. Thus, it simplifies the designation of the optical measuring device and lowers the cost. Furthermore, the invention can perform measurement and correction based on the existing framework of the optical measuring device. It merely needs to introduce correction into the processing unit but it outstandingly improves measurement precision on condition that no additional correction unit is necessary to install and no existing device will be replaced. Thus, it is beneficial and effective.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. An optical measuring device, comprising:
   a first light source module, providing a first light beam;
   a second light source module, providing a second light beam;
   a first sensing unit;
   a second sensing unit;
   a reference mirror set, having an actuator and a reference mirror, wherein the actuator drives the reference mirror to move back and forth at a scan velocity;
   an optical coupling module, transmitting the first light beam to the reference mirror set and an examinee object; and
   a processing unit;
   wherein the first light source module transmits the first light beam to the optical coupling module, the optical coupling module transmits one part of the first light beam to the examinee object, and the other one part of the first light beam to the reference mirror set, the one part of the first light beam is reflected by the surface of the examinee object and then transmitted to the optical coupling module, the first sensing unit and the processing unit in sequence, the other one part of the first light beam is reflected by the reference mirror set and then transmitted to the optical coupling module, the first sensing unit and the processing unit in sequence;
   wherein the second light source module transmits a second light beam to the examinee object, the second light beam is reflected by the surface of the examinee object and then transmitted to the second sensing unit, the second sensing unit accordingly provides a sensing signal to the processing unit, the processing unit provides a value of a relative velocity, calculates the thickness according to the scan velocity of the reference mirror set and the value of the relative velocity.

2. The optical measuring device of claim 1, wherein the thickness is generated according to the integration of the fraction being the sum of the scan velocity and the value of the relative velocity with respect to the refractive index of the examinee object.

3. The optical measuring device of claim 2, wherein the processing unit utilizes the following formula to calculate the thickness L:

$$L = \int_0^T \frac{Vr + Vs}{n} dt$$

wherein $V_r$ represents the scan velocity, $V_S$ represents the value of the relative velocity, n represents the refractive index of the examinee object.

4. The optical measuring device of claim 1, wherein the processing unit utilizes the following formula to calculate the thickness L:

$$L = \int_0^T \frac{Vr}{n} * \left\{1 + \left(\sqrt{\frac{1+\beta}{1-\beta}} - 1\right) \middle/ n\right\} dt$$

$$\beta = \frac{n * Vs}{Vr}$$

wherein $V_r$ represents the scan velocity, $V_S$ represents the value of the relative velocity, n represents the refractive index of the examinee object.

5. The optical measuring device of claim 1, wherein, during a first time sequence, the first light beam reflected by the examinee object and the first light beam reflected by the reference mirror set produce constructive interference, and the processing unit accordingly provides a first optical path difference;

during a second time sequence, the first light beam reflected by the examinee object and the first light beam reflected by the reference mirror set produce constructive interference, and the processing unit accordingly provides a second optical path difference;

the processing unit calculates the time interval between the first time sequence and the second time sequence according to the first and the second optical path differences.

6. An optical measuring method for an optical measuring device, wherein a reference mirror set of the optical measuring device has a scan velocity, the method comprising:

providing a light beam to a surface of an examinee object;

reflecting the light beam by the surface of the examinee object and being transmitted to a sensing unit;

transmitting a sensing signal to a processing unit by the sensing unit, wherein the sensing signal includes information about the scanning velocity of the light beam;

providing a value of a relative velocity between the optical measuring device and the examinee object according to the sensing signal; and calculating a thickness of the examinee object according to the value of the relative velocity and the scan velocity.

7. The optical measuring method of claim 6, further comprising:

calculating the thickness according to the integration of the fraction being the sum of the scan velocity and the value of the relative velocity with respect to the refractive index of the examinee object.

8. The optical measuring method of claim 7, wherein the thickness L is:

$$L = \int_0^T \frac{Vr + Vs}{n} dt$$

wherein $V_r$ represents the scan velocity, $V_S$ represents the value of the relative velocity, n represents the refractive index of the examinee object.

9. The optical measuring method of claim 6, wherein the thickness L is:

$$L = \int_0^T \frac{Vr}{n} * \left\{1 + \left(\sqrt{\frac{1+\beta}{1-\beta}} - 1\right) \middle/ n\right\} dt$$

$$\beta = \frac{n * Vs}{Vr}$$

wherein $V_r$ represents the scan velocity, $V_S$ represents the value of the relative velocity, n represents the refractive index of the examinee object.

* * * * *